US 6,657,080 B2

(12) United States Patent
Yunoki

(10) Patent No.: US 6,657,080 B2
(45) Date of Patent: Dec. 2, 2003

(54) PROCESS FOR PRODUCING ACRYLIC ACID

(75) Inventor: Hiromi Yunoki, Himeji (JP)

(73) Assignee: Nippon Shokukai Co. Ltd, Osaka (JP)

( * ) Notice: Subject to any disclaimer, the term of this patent is extended or adjusted under 35 U.S.C. 154(b) by 0 days.

(21) Appl. No.: 09/878,421

(22) Filed: Jun. 12, 2001

(65) Prior Publication Data

US 2003/0060659 A1 Mar. 27, 2003

(30) Foreign Application Priority Data

Jun. 12, 2000 (JP) .................................. 2000-175043

(51) Int. Cl.$^7$ .............................................. C07C 51/235
(52) U.S. Cl. .................. 562/532; 562/534; 562/535
(58) Field of Search ................. 562/532, 534, 562/535

(56) References Cited

U.S. PATENT DOCUMENTS

| 3,801,634 | A | * | 4/1974 | Krabetz et al. ............. 562/532 |
| 4,031,135 | A | * | 6/1977 | Engelbach et al. ......... 562/535 |
| 4,365,087 | A | * | 12/1982 | Kadowaki et al. .......... 562/534 |
| 4,837,360 | A | | 6/1989 | Kadowaki |
| 4,873,368 | A | * | 10/1989 | Kadowaki et al. .......... 562/532 |
| 5,264,625 | A | * | 11/1993 | Hammon et al. ............ 562/532 |
| 5,719,318 | A | * | 2/1998 | Kawajiri et al. ............. 562/532 |

FOREIGN PATENT DOCUMENTS

| EP | 0 614 868 | 9/1994 |
| EP | 0 792 866 | 9/1997 |

* cited by examiner

*Primary Examiner*—Alan L. Rotman
*Assistant Examiner*—Taylor V Oh
(74) *Attorney, Agent, or Firm*—Sherman & Shalloway

(57) ABSTRACT

The invention provides a process which, in producing acrylic acid through vapor-phase catalytic oxidation of acrolein-containing gas using a shell-and-tube type fixed bed reactor, can effectively inhibit occurrence of hot spots and produce acrylic acid at high yields. Said process is characterized by dividing each of the reaction tubes into at least three reaction zones in its axial direction, filling the first reaction zone closest to the gas inlet with a catalyst having a higher activity than that of the catalyst filling the adjacent, second reaction zone and filling the subsequent reaction zones with catalysts of different activity levels such that the catalytic activity successively rises from the second reaction zone toward the gas outlet side.

2 Claims, No Drawings

PROCESS FOR PRODUCING ACRYLIC ACID

TECHNICAL FIELD TO WHICH THE INVENTION BELONGS

This invention relates to an improvement in a process for producing acrylic acid by vapor-phase catalytic oxidation of an acrolein-containing gas.

CONVENTIONAL TECHNOLOGY

In such production process of acrylic acid, for the purpose of enhancing productivity of acrylic acid, such means as increasing concentration of the starting material or increasing space velocity of the gaseous material are adopted in recent years. Under those heavy load conditions, however, the temperature at hot spots in the catalyst layers rises high because the vapor-phase catalytic oxidation is an extremely exothermic reaction, to induce over-oxidation. In consequence, acrylic acid yield drops and thermal degradation of the catalyst is accelerated, in the worst case even causing a run-away reaction. Therefore, currently the process is under considerable restrictions in respect of the reaction conditions.

Various methods have been proposed to solve this problem, which proposals include, for example: ① Japanese Patent Publication Sho 53(1978)-30688B1 (=U.S. Pat. No. 3,801,634) proposed a method comprising diluting the catalyst with an inert substance; ② Japanese Patent Publication Hei 9(1997)-241209A1 (=U.S. Pat. No. 5,719,318) proposed a method comprising changing the catalyst size; and ③ Japanese Patent Publication Hei 7(1995)-10802A1, a method comprising changing the carriage ratio of catalytically active component (weight ratio of the active substance per unit weight of the catalyst).

These methods basically adopt a means of dividing reaction tubes into plural reaction zones in their axial direction and filling the reaction zones with catalysts such that the catalytic activity successively increases from the gas inlet side toward the outlet side. In these methods, however, reactivity of the starting material tends to decrease because activity of the catalyst disposed at the gas inlet side is set at a low level. For overcoming this defect and obtaining an industrially advantageous high reactivity, such countermeasures as increasing the total catalyst layer length or raising the reaction temperature are required.

Extending the catalyst layer length, however, invites a disadvantage that pressure loss at the catalyst layer increases, and moreover necessitates to enlarge the reactor. Thus the method cannot be economically advantageous. Where the reaction temperature is raised, on the other hand, thermal degradation of the catalyst is accelerated to adversely affect the catalyst life, similarly to the case wherein the hot spot temperature becomes high. Besides, there rises an additional problem that side products increase to reduce yield of the object product. In particular, where the reaction is carried out under such heavy load conditions as increased concentration of the starting material or higher space velocity, catalyst of still lower activity level must be disposed at the reactant gas inlet side to suppress the hot spot temperature, which renders these problems even more serious.

On the other hand, a reactant gas introduced into a catalyst layer in a reactor in industrial working of the vapor-phase catalytic oxidation generally has a temperature lower than the reaction temperature. For satisfactory and efficient catalytic performance, however, the temperature of the reactant gas which is introduced into the catalyst layer needs to be raised to the reaction temperature level. As a method of heating a reactant gas to a predetermined reaction temperature, it is known to provide a pre-heating zone formed of an inert substance at the reactant gas inlet side of the reaction tubes. However, provision of such an inert substance layer, which does not participate in the reaction, in the reaction tubes of a limited length is quite inefficient. Whereas, when no pre-heating zone is provided or the pre-heating zone is short, in the conventional process disposing a catalyst of the lowest activity level at the reactant gas inlet side, the catalyst takes nearly no part in the oxidation reaction during its contact with the reactant gas having a temperature lower than the reaction temperature. This amounts to utilization of costly catalyst simply as a pre-heating zone, which obviously is ineconomical.

PROBLEM TO BE SOLVED BY THE INVENTION

Accordingly, the object of the invention is to provide a process for producing acrylic acid at high yield stably over a prolonged period, by efficiently inhibit occurrence of hot spots during production of acrylic acid through vapor-phase catalytic oxidation of acrolein-containing gas.

MEANS FOR SOLVING THE PROBLEM

I have discovered: when each reaction tube in a shell-and-tube type fixed bed reactor is divided into at least three reaction zones (catalyst layers), forming sequentially the first, second, third . . . reaction zones from the gas inlet side toward the gas outlet side and filling the second reaction zone with a catalyst of the lowest activity level among plural catalysts exhibiting different activity levels which are advancely prepared, in other words, when a catalyst of a higher activity level is disposed in the reaction zone closest to the gas inlet, the reaction temperature can be lowered even in the reaction under heavy load conditions and hot spot temperature does not rise inconveniently, in consequence enabling the reaction to continue with stability. I have furthermore discovered that the disposition of a catalyst of higher activity level at the gas inlet side enables the catalysts to exhibit their performance with high efficiency even when the pre-heating zone is shorter than that in conventional processes or no pre-heating zone is provided, and in consequence gives the object product at high yield without lowering reactivity of the starting raw material.

Accordingly, therefore, the invention provides a production process of acrylic acid comprising vapor-phase catalytic oxidation of acrolein-containing gas using a shell-and-tube type fixed bed reactor, said process being characterized by dividing each of the reaction tubes into at least three reaction zones in its axial direction, filling the first reaction zone closest to the gas inlet with a catalyst having a higher activity than that of the catalyst filling the adjacent, second reaction zone and filling the subsequent reaction zones with catalysts of different activity levels such that the catalyst activity successively rises from the second reaction zone toward the gas outlet side.

WORKING EMBODIMENTS OF THE INVENTION

According to the invention, each reaction tube in a shell-and-tube type fixed bed reactor is divided into at least three reaction zones in the axial direction of said tube, and the reaction zones are filled with catalyst layers in the above-described mode. While the more number of the reaction zones (catalyst layers), the easier to control the temperature rise at hot spots, for industrial practice provision of three reaction zones (catalyst layers) is normally sufficient for achieving the intended effect.

The ratios between individual lengths of said three or more reaction zones (catalyst layers), which are formed by dividing individual reaction tube in its axial direction, and the total length of said plural reaction zones (catalyst layers) is variable depending on the reaction conditions, catalyst activity levels and the like and cannot be generally specified. Whereas, when the number of the reaction zones (catalyst layers) is three, for example, the ratios can be set up, for example, in the following manner: the ratio ($L_1/L$) between the length ($L_1$) of the first reaction zone (the first catalyst layer) and the total length (L) of the reaction zones (catalyst layers) is normally selected to satisfy the condition expressed by the following formula $$0 < \frac{L_1}{L} \leq 0.5,$$

$$\text{preferably } 0 < \frac{L_1}{L} \leq 0.2,$$

$$\text{inter alia } 0 < \frac{L_1}{L} \leq 0.1;$$

the ratio ($L_2/L$) between the length ($L_2$) of the second reaction zone (the second catalyst layer) and the total length (L), to satisfy the condition expressed by $$\text{normally, a formula } 0 < \frac{L_2}{L} \leq 0.6,$$

$$\text{preferably } 0.05 < \frac{L_2}{L} \leq 0.5,$$

$$\text{inter alia } 0.1 \leq \frac{L_2}{L} \leq 0.4;$$

provided that $L_1/L + L_2/L$ is less than 1. The ratio ($L_3/L$) between the length ($L_3$) of the third reaction zone (the third catalyst layer) and the total length (L) is selected to satisfy the following formula, $$\frac{L_3}{L} = 1 - \left(\frac{L_1}{L} + \frac{L_2}{L}\right).$$

In setting the above ratios, care should be taken to such facts that an excessively high $L_1/L$ value tends to raise hot spot temperature due to over-oxidation, and an excessively low $L_1/L$ value tends to reduce the effect of filling the first reaction zone with a catalyst of high activity level.

According to the invention, plural catalysts having different levels of the catalytic activity are prepared, and the one of the lowest activity level is filled in the second reaction zone. The reaction zones subsequent to the second reaction zones are filled with the catalysts such that the activity level rises successively from the second reaction zone. The catalysts per se are not subject to any critical limitations, but any of those generally used in acrylic acid production through vapor-phase catalytic oxidation of an acrolein-containing gas can be used. More specifically oxides or complex oxides which are expressed by the following general formula (1) are conveniently used as the catalysts:

  (1)

(wherein Mo is molybdenum; V is vanadium; W is tungsten; Cu is copper; A is at least an element selected from the group consisting of zirconium, titanium and cerium; B is at least an element selected from a group consisting of magnesium, calcium, strontium and barium; C is at least an element selected from the group consisting of niobium, antimony, tin, tellurium, phosphorus, cobalt, nickel, chromium, manganese, zinc and bismuth; D is at least an element selected from alkali metals; and O is oxygen; and where a is 12, b, c, d, e, f, g and h are, respectively, $1 \leq b \leq 14$, $0 < c \leq 12$, $0 < d \leq 6$, $0 \leq e \leq 10$, $0 \leq f \leq 3$, $0 \leq g \leq 10$ and $0 \leq h \leq 5$, and i is a numerical value determined by degree of oxidation of each of the elements).

The catalysts of the above general formula (1) can be prepared by any methods which are generally practiced for preparing this type of catalysts.

The catalysts to be used in the invention may be molded catalysts formed by molding the catalytic components into a predetermined shape; carrier-supported catalysts in which the catalytic components are carried on an optional inert carrier having a fixed shape; or such molded catalyst may be used in combination with carrier-supported catalyst.

Those shaped catalysts can be suitably prepared by customarily used shaping methods such as extrusion-molding, tabletting and the like. The supported catalysts can be prepared by having the catalytically active components carried on an inert carrier following accepted practices. Examples of useful inert carrier include alumina, silica, silica-alumina, titania, magnesia, silica-magnesia, steatite, silicon carbide, silicon nitride and zeolite.

The shape of the catalysts is subject to no critical limitation, and any optional shape such as columnar, ring, spherical and what else can be selected. Obviously, when it is spherical, it is unnecessary to be true sphere but may be substantially spherical. Shapes of the catalysts to fill each of the reaction zones may be same or different.

The term, "activity", as used in relation to this invention signifies the catalyst's performance for acrolein conversion. Hence, a catalyst showing a higher (or lower) acrolein conversion is referred to as a catalyst having a higher (or lower) activity.

The method for preparing plural catalysts showing different activity levels which are used in the invention is subject to no critical limitations but generally well known means can be used. Some of typical means are listed in the following, which may be used either singly or in combination:

(1) adjustment of kind and/or amount of the catalytically active components, (2) adjustment of occupation volume of the catalysts, (3) where supported catalysts are used, adjustment of the carried amount of the catalytically active components, (4) adjustment of calcination temperature at the time of catalyst preparation.

The vapor-phase oxidation reaction of an acrolein-containing gas according to the invention can be conducted under the conditions normally used for this kind of reaction. For example, the reaction can be carried out by contacting a starting gas composed of a gaseous mixture comprising 1–15 volume % of acrolein, 1–10 volume times thereof of molecular oxygen and the balance of a diluent inert gas such as nitrogen, carbon dioxide and steam (steam being utilized with particular advantage because it inhibits formation of side-products and improves yield of the object product) with the catalysts at a temperature range of 220–450° C. under a pressure range of 0.1–1 MPa and at a space velocity of 300–5000 h$^{-1}$ (STP).

As the gaseous starting material, an acrolein-containing gaseous mixture which is obtained from oxidation of propylene can also be used in place of the above gaseous mixture of acrolein, oxygen and inert gas. It is permissible to add to such an acrolein-containing gaseous mixture, if required, air or oxygen, and steam. Components other than acrolein that are contained in said gaseous mixture, such as acrylic acid, acetaldehyde, acetic acid, carbon dioxide, propane and propylene, are in no way detrimental to working of the present invention.

EFFECTS OF THE INVENTION

According to the invention, the following effects are achieved.

(1) The reaction temperature and ΔT (catalyst layer hot spot temperature) can be lowered even under heavy load operating conditions such as high raw material concentration and high space velocity, and in consequence:

(a) acrylic acid yield improves, and (b) thermal deterioration of the catalyst is suppressed to enable stable use of the catalyst over a prolonged period;

(2) because provision of a pre-heating zone can be dispensed with, or of only a short pre-heating zone is sufficient, pressure loss is decreased, consequently rendering the reactor size compact to reduce production costs including equipment costs.

Thus, the process of the invention is very useful for industrial vapor-phase catalytic oxidation reaction.

EXAMPLES

Hereinafter the present invention is explained more specifically referring to working Examples, it being understood that the invention is in no way thereby limited. In the Examples, conversion, selectivity and acrylic acid yield are defined by the following equations, respectively:

$$\text{Conversion (mol \%)} = \frac{\text{(mol number of reacted acrolein/}}{\text{mol number of sup-plied acrolein)}} \times 100$$

$$\text{Selectivity (mol \%)} = \frac{\text{(mol number of formed acrylic acid/}}{\text{mol number of reacted acrolein)}} \times 100$$

$$\text{Yield (mol \%)} = \frac{\text{(mol number of formed acrylic acid/}}{\text{mol number of supplied acrolein)}} \times 100$$

Referential Example 1
(Catalyst Preparation)

Into 4000 ml of water, 676 g ammonium molybdate, 224.0 g of ammonium metavanadate and 103.4 g of ammonium paratungstate were dissolved under heating and stirring. Separately, 192.7 g of copper nitrate was dissolved in 200 ml of water under heating and stirring. Thus formed two aqueous solutions were mixed, and into the resulting mixture 63.7 g of titanium dioxide and 46.5 g of antimony trioxide were further added, to provide a suspension (i). Said suspension (i) was given continuous heating and stirring until evaporated to a dry solid, and the solid blocks were further dried in a dryer at 120° C. for 5 hours, followed by grinding to provide a powder (ii) of about 100 mesh in particle size. The powder (ii) was shaped to columns of each 5 mm in diameter and 5 mm in height with a tablet-molding machine, which were heat-treated at 400° C. for 6 hours in air to provide a catalyst (1). The metallic elementary composition of this catalyst (1) excepting oxygen was as follows:

$Mo_{12}V_6W_{1.2}Cu_{2.5}Sb_1Ti_{2.5}$.

(Oxidation Reaction)

A stainless steel reaction tube of 25 mm in inner diameter which had been heated with molten salt was filled with inert alumina balls of 5 mm in average diameter over a layer length of 200 mm on the upstream side from the gas inlet side to provide a pre-heating layer and on the down stream side thereof with above catalyst (1) over a layer length of 1,000 mm. Through the reaction tube a starting material gas having the following composition was passed at a space velocity of 1800 hr$^{-1}$ for 50 hours, to conduct vapor-phase catalytic oxidation of acrolein. The result was as shown in Table 1.

Composition of the Material Gas:

| | |
|---|---|
| Acrolein | 5 volume % |
| Air | 20 volume % |
| Steam | 30 volume % |
| Inert gas composed mainly of nitrogen | 45 volume % |

Referential Example 2

The powder (ii) was obtained by the procedures identical with Referential Example 1. Steatite carrier balls of 5 mm in diameter were thrown into a centrifugal flow coater, and successively the powder (ii) was thrown into the same coater, together with distilled water which served as a binder, while passing hot air of 90° C. there-through. The catalyst thus supported on the carrier was heat-treated at 400° C. for 6 hours in air, to provide a catalyst (2). The carriage ratio of the catalytically active components of said catalyst (2) was 30%. The oxidation reaction was carried out similarly to Referential Example 1, using the catalyst (2). The result was as shown in Table 1.

Referential Example 3

The suspension (i) was prepared by the procedures identical with Referential Example 1, which was placed in a porcelain evaporator on a hot water bath and stirred with 2500 g of silica-alumina carrier balls of 5 mm in diameter to evaporate off the water component, leaving dry solid. After so depositing the catalytically active components on the carrier, the solid was further heat-treated at 400° C. for 6 hours in air to provide a catalyst (3). The carriage ratio of the catalytically active components of this catalyst (3) was 25%. The oxidation reaction was carried out similarly to Referential Example 1, using the catalyst (3). The result was as shown in Table 1.

Referential Example 4

A catalyst (4) was prepared in identical manner with Referential Example 1, except that 6.5 g of potassium nitrate was added during preparation of the suspension (i). The carriage ratio of the catalytically active components of this catalyst (4) was 25%, and the metallic elementary composition excepting oxygen was as follows:

$Mo_{12}V_6W_{1.2}Cu_{2.5}Sb_1Ti_{2.5}K_{0.2}$.

The oxidation reaction was carried out similarly to Referential Example 1, using the catalyst (4). The result was as shown in Table 1.

Referential Example 5

Referential Example 3 was repeated except that silica-alumina carrier balls of 8 mm in diameter were used, to provide a catalyst (5). The carriage ratio of the catalytically active components of this catalyst (5) was 25%. The oxidation reaction was carried out similarly to Referential Example 1, using the catalyst (5). The result was as shown in Table 1.

TABLE 1

| | Cata-lyst No. | Catalyst Composition [shape and dimension: heat-treating temp.] | Reaction Temp. (° C.) | Acrolein Conversion (mol %) | Acrylic Acid Selectivity (mol %) | Acrylic Acid Yield (mol %) |
|---|---|---|---|---|---|---|
| Referential Example 1 | (1) | $Mo_{12}V_6W_{1.2}Cu_{2.5}Sb_1Ti_{2.5}$ [tablet (5 × 5 mm); 400° C.] | 240 | 99.9 | 90.3 | 90.2 |
| Referential Example 2 | (2) | $Mo_{12}V_6W_{1.2}Cu_{2.5}Sb_1Ti_{2.5}$ [supported (5 mm diameter: 30%); 400° C.] | 240 | 99.4 | 94.7 | 94.1 |
| Referential Example 3 | (3) | $Mo_{12}V_6W_{1.2}Cu_{2.5}Sb_1Ti_{2.5}$ [supported (5 mm diameter: 25%); 400° C.] | 240 | 98.8 | 95.6 | 94.5 |
| Referential Example 4 | (4) | $Mo_{12}V_6W_{1.2}Cu_{2.5}Sb_1Ti_{2.5}K_{0.2}$ [supported (5 mm diameter: 25%); 400° C.] | 240 | 94.6 | 96.2 | 91.0 |
| Referential Example 5 | (5) | $Mo_{12}V_6W_{1.2}Cu_{2.5}Sb_1Ti_{2.5}K_{0.2}$ [supported (8 mm diameter: 25%); 400° C.] | 240 | 91.0 | 96.6 | 87.9 |

As is clear from the acrolein conversion values of Referential Examples 1–5 given in Table 1, in respect of the catalytic activity the catalyst (1) is the highest, and the catalyst (2), catalyst (3), catalyst (4) and catalyst (5) show successively lower values.

Example 1

A stainless steel reaction tube of 25 mm in inner diameter, which had been heated with molten salt, was filled, sequentially from the gas inlet side toward the outlet side, with a pre-heating layer (alumina balls of 5 mm in average diameter) over a length of 200 mm; with catalyst (1) over a length of 150 mm; with catalyst (5) over a length of 1,000 mm; and with catalyst (3), over a length of 1850 mm. Through said tube a gaseous starting material of the following composition was passed at a space velocity of 2000 $hr^{-1}$ continuously for 4000 hours, to conduct vapor-phase catalytic oxidation of acrolein. The catalytic performance at the initial stage of the reaction (50 hours from the start) and after 4000 hours' operation were as shown in Table 2.

Composition of Gaseous Material:

| | |
|---|---|
| Acrolein | 7 volume % |
| Air | 35 volume % |
| Steam | 15 volume % |
| Inert gas composed mainly of nitrogen | 43 volume %. |

Examples 2–5

The reaction was continuously conducted for 4000 hours similarly to Example 1, except that the pre-heating layer and the catalyst layers filling the reaction tube were varied for each run as indicated in Table 2. The catalytic performance at the initial stage of the reaction and after 4000 hours were as shown in Table 2.

Comparative Examples 1–4

The reaction was carried out similarly to Example 1, except that the pre-heating layer and the catalyst layers were filled as shown in Table 2. As for Comparative Example 1, the reaction was continuously run for 4000 hours and the catalytic performance at the initial stage of reaction and after the 4000 hours' reaction is shown in Table 2.

TABLE 2

| | Pre-heating layer length | Different Catalyst Layers Filled from Gas-inlet Side toward Outlet Side and Their Lengths | Reaction Time (hr) | Reaction Temp. (° C.) | Hot Spot Temp. (° C.) | Acrolein Conversion (mol %) | Acrylic Acid Selectivity (mol %) | Acrylic Acid Yield (mol %) |
|---|---|---|---|---|---|---|---|---|
| Example 1 | 200 mm | catalyst (1)/catalyst (5)/catalyst (3) 150 mm/1000 mm/1850 mm | initial stage | 245 | 326 | 99.3 | 93.8 | 93.1 |
| | | | | 240 | 312 | 98.9 | 95.0 | 94.0 |
| | | | after 4000 h | 245 | 305 | 98.9 | 95.2 | 94.2 |
| Example 2 | 200 mm | catalyst (2)/catalyst (5)/catalyst (3) 200 mm/800 mm/2000 mm | initial stage | 240 | 308 | 99.1 | 95.2 | 94.3 |
| | | | after 4000 h | 244 | 302 | 99.0 | 95.3 | 94.3 |
| Example 3 | 200 mm | catalyst (2)/catalyst (5)/catalyst (2) 250 mm/750 mm/2000 mm | initial stage | 240 | 312 | 99.4 | 94.3 | 93.7 |
| | | | after 4000 h | 243 | 305 | 99.2 | 94.9 | 94.1 |
| Example 4 | 200 mm | catalyst (4)/catalyst (5)/catalyst (3) 350 mm/600 mm/2050 mm | initial stage | 245 | 319 | 99.3 | 95.0 | 94.3 |
| | | | after 4000 h | 249 | 309 | 99.0 | 95.5 | 94.5 |
| Comparative Example 1 | 200 mm | catalyst (5)/catalyst (3) 1000 mm/2000 mm | initial stage | 245 | 321 | 98.7 | 94.3 | 93.1 |
| | | | after 4000 h | 253 | 318 | 98.8 | 94.6 | 93.5 |
| Comparative Example 2 | 200 mm | catalyst (5)/catalyst (3)/catalyst (1) 1000 mm/1850 mm/150 mm | initial stage | 245 | 319 | 98.7 | 94.2 | 93.0 |
| Comparative Example 3 | 200 mm | catalyst (3)/catalyst (5) 1000 mm/2000 mm | initial stage | 245 | | The reaction was stopped because of drastic rise in hot spot temperature. | | |
| | | | | 240 | | | | |
| Example 5 | 0 mm * | catalyst (1)/catalyst (5)/catalyst (3) | initial stage | 245 | 320 | 99.0 | 93.9 | 93.0 |

TABLE 2-continued

| | Pre-heating layer length | Different Catalyst Layers Filled from Gas-inlet Side toward Outlet Side and Their Lengths | Reaction Time (hr) | Reaction Temp. (° C.) | Hot Spot Temp. (° C.) | Acrolein Conversion (mol %) | Acrylic Acid Selectivity (mol %) | Acrylic Acid Yield (mol %) |
|---|---|---|---|---|---|---|---|---|
| Comparative Example 4 | 0 mm * | 150 mm /1000 mm/1850 mm catalyst (5)/catalyst (3) 1000 mm/2000 mm | initial stage | 240 245 | 305 315 | 98.5 98.0 | 95.2 94.6 | 93.8 92.7 |

* No pre-heating layer provided

It is understood from Table 2 that Examples 1–5 in which the catalysts were disposed according to the present invention showed reduction in reaction temperature and hot spot temperature in the catalyst layer and higher acrylic acid yield, compared to Comparative Examples 1–4 in which the catalysts were disposed such that the catalytic activity monotonously rose from the gas inlet side toward the outlet side.

Example 6

A gaseous mixture composed of propylene (industrial propylene of 95% in purity), 8 vol. %; oxygen, 15 vol. %; steam, 10 vol. %; and nitrogen, 66.6 vol. %; was catalytically oxidized at vapor phase in the presence of a catalyst for propylene oxidation whose essential components were molybdenum, bismuth and iron. Thus obtained acrolein-containing gaseous mixture was introduced into a reaction tube filled with a pre-heating layer and the catalyst layers in the manner identical with Example 1, and subjected to the oxidation reaction at the reaction temperature of 250° C. and a space velocity of 2000 h$^{-1}$.

When calculated under an assumption that the propylene, propane, acrylic acid, acetic acid and other by-products which were contained in the acrolein-containing gaseous mixture which was introduced into the reaction tube did not participate in the reaction, the acrolein conversion in this reaction was 99.3%, acrylic acid selectivity was 95.5% and acrylic acid yield was 94.8%.

What is claimed is:

1. A process for producing acrylic acid comprising vapor-phase catalytic oxidation of acrolein-containing gas using a shell-and-tube fixed bed reactor, said process being characterized by dividing each of the reaction tubes into three reaction zones in its axial direction, filling the first reaction zone closest to the gas inlet with a catalyst having a higher activity expressed in acrolein conversion as a mol % than that of the catalyst filling the adjacent, second reaction zone and filling the subsequent reaction zones with catalysts of different activity levels such that the catalyst activity successively rises from the second reaction zone toward the gas outlet side wherein said catalysts are formed of oxides or complex oxides expressed by the following general formula (1)

$$Mo_aV_bW_cCu_dA_eB_fC_gD_hO_i \qquad (1)$$

wherein Mo is molybdenum; V is vanadium; W is tungsten; Cu is copper; A is selected from the group consisting of zirconium, titanium and cerium; B is selected from the group consisting of magnesium, calcium, strontium and barium; C is selected from the group consisting of niobium, antimony, tin, tellurium, phosphorus, cobalt, nickel, chromium, manganese, zinc and bismuth; D is selected from alkali metals; and O is oxygen; and where a is 12, b, c, d, e, f, g and h are respectively, $1 \leq b \leq 14$, $0 < c \leq 12$, $0 < d \leq 6$, $0 \leq e \leq 10$, $0 \leq f \leq 3$, $0 \leq g \leq 10$ and $0 \leq h \leq 5$, and i is a numerical value determined by degree of oxidation of each of the elements.

2. The process for producing acrylic acid according to claim 1, in which each of the reaction tubes is divided into three reaction zones in the axial direction of the tube, the ratio ($L_1/L$) between the length ($L_1$) of the first reaction zone and the total length (L) of the reaction zones being selected to satisfy the condition expressed by the following formula $$0 < \frac{L_1}{L} \leq 0.5,$$

the ratio ($L_2/L$) between the length ($L_2$) of the second reaction zone and the total length (L), to satisfy the condition expressed by a formula $$0 < \frac{L_2}{L} \leq 0.6,$$

provided that $L_1/L + L_2/L$ is less than 1; and the ratio ($L_3/L$) between the length ($L_3$) of the third reaction zone and the total length (L) being selected to satisfy the following formula, $$\frac{L_3}{L} = 1 - \left(\frac{L_1}{L} + \frac{L_2}{L}\right).$$

* * * * *

UNITED STATES PATENT AND TRADEMARK OFFICE
CERTIFICATE OF CORRECTION

PATENT NO.    : 6,657,080 B2
DATED         : December 2, 2003
INVENTOR(S)   : Hiromi Yunoki It is certified that error appears in the above-identified patent and that said Letters Patent is hereby corrected as shown below:

<u>Title page,</u>
Item [73], change "[73] Assignee: Nippon Shokukai Co. Ltd, Osaka (JP)" to
-- [73] Assignee: Nippon Shokubai Co., Ltd., Osaka (JP) --

Signed and Sealed this

Thirteenth Day of April, 2004

JON W. DUDAS
*Acting Director of the United States Patent and Trademark Office*